(12) United States Patent
Chan

(10) Patent No.: US 6,562,043 B1
(45) Date of Patent: *May 13, 2003

(54) APPARATUS AND METHOD FOR LIGAMENT FIXATION

(76) Inventor: Kwan-Ho Chan, 4803 1st Pl., Lubbock, TX (US) 79410

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/315,918

(22) Filed: May 20, 1999

Related U.S. Application Data

(60) Provisional application No. 60/086,329, filed on May 21, 1998, and provisional application No. 60/125,745, filed on Mar. 23, 1999.

(51) Int. Cl.$^7$ ............................................... A61B 17/56
(52) U.S. Cl. ........................................................ 606/65
(58) Field of Search .............................. 606/60, 62, 63, 606/64, 72, 73; 623/13

(56) References Cited

U.S. PATENT DOCUMENTS

| | | | | |
|---|---|---|---|---|
| 4,870,957 A | * | 10/1989 | Goble et al. ................... | 606/73 |
| 5,324,308 A | * | 6/1994 | Pierce .......................... | 606/72 |
| 5,372,599 A | * | 12/1994 | Martins ........................ | 606/72 |
| 5,383,878 A | * | 1/1995 | Roger et al. .................. | 606/72 |
| 5,464,427 A | * | 11/1995 | Curtis et al. ................... | 606/72 |
| 5,632,748 A | * | 5/1997 | Beck et al. .................... | 606/72 |
| 5,728,136 A | * | 3/1998 | Thal ............................. | 606/73 |
| 5,766,250 A | * | 6/1998 | Chervitz et al. ............... | 623/13 |
| 5,849,004 A | * | 12/1998 | Bramlet ........................ | 606/72 |
| 5,931,869 A | * | 8/1999 | Boucher et al. ............... | 623/13 |
| 6,264,691 B1 | | 7/2001 | Weiler | |

FOREIGN PATENT DOCUMENTS

| WO | 94028799 | * 12/1994 | .................. 606/72 |
|---|---|---|---|

* cited by examiner

Primary Examiner—Eduardo C. Robert
(74) Attorney, Agent, or Firm—Pandiscio & Pandiscio

(57) ABSTRACT

A jamming retainer for fixing a ligament in a bone tunnel without excessive sideways pressure on the ligament that may result in tissue necrosis, the jamming retainer including a substantially rigid body with a bore or loop for receiving a ligament or tendon and a bore or ring for receiving a suture for towing the jamming retainer and ligament or tendon through a bone tunnel. Once positioned, the jamming retainer is fixed in the bone tunnel with an interference screw.

1 Claim, 13 Drawing Sheets

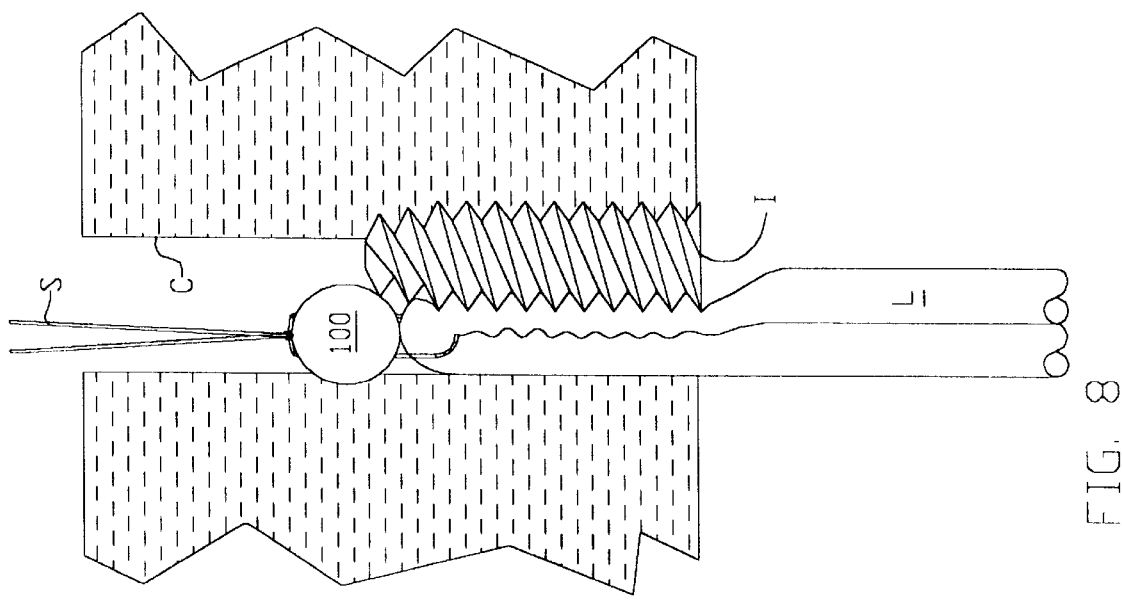
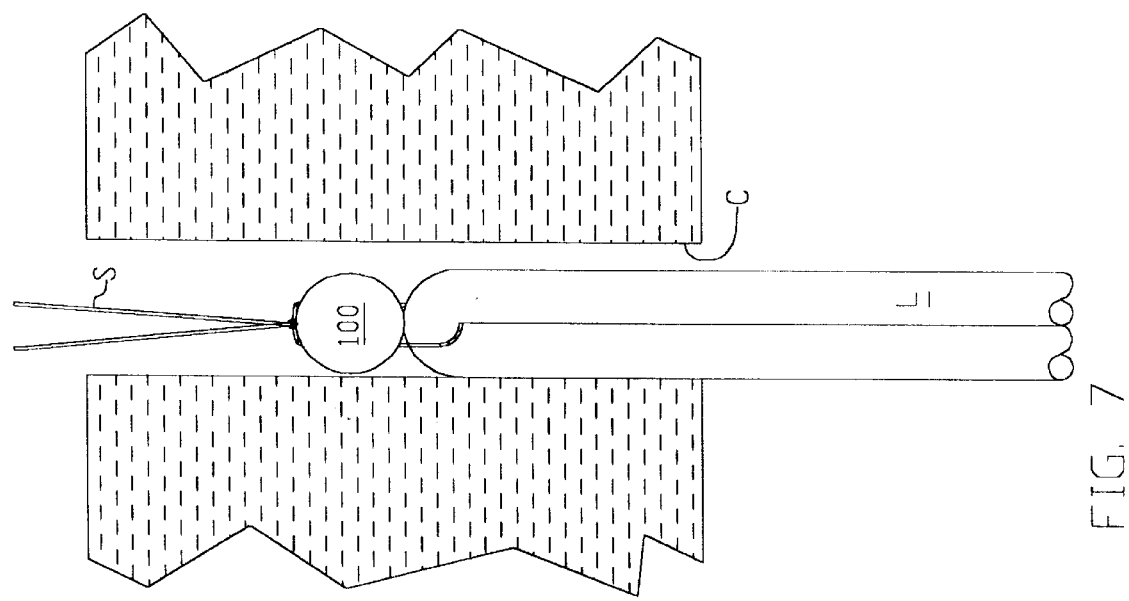

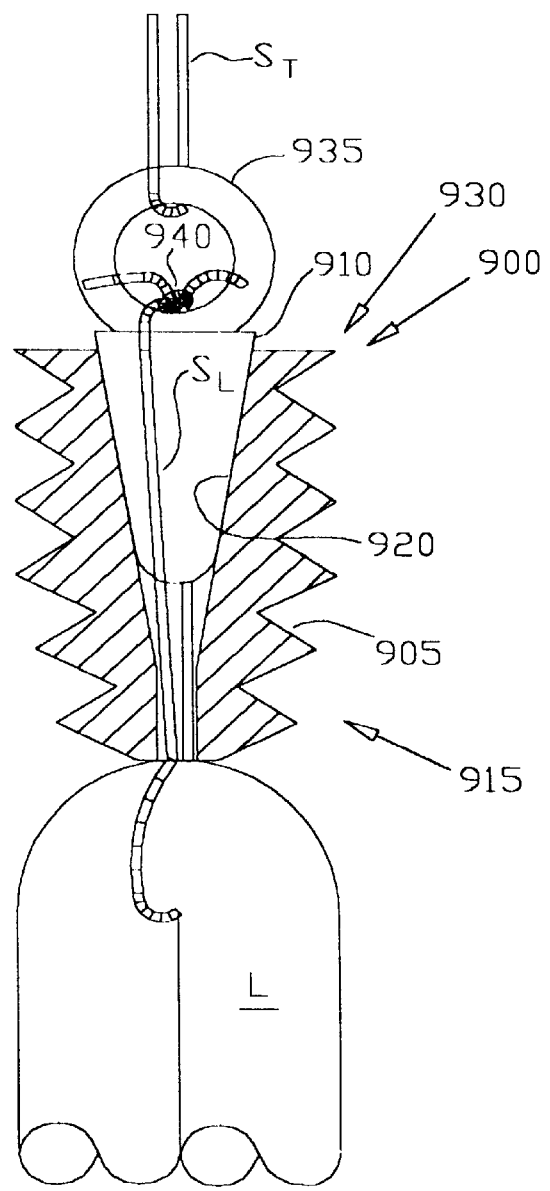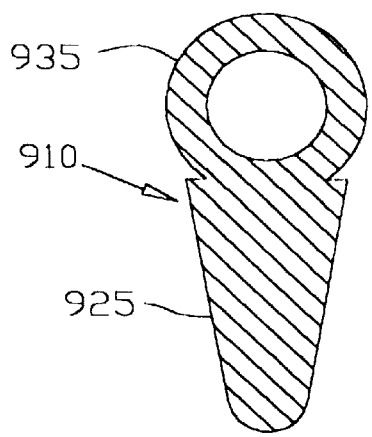
FIG. 27
FIG. 28

APPARATUS AND METHOD FOR LIGAMENT FIXATION

REFERENCE TO EARLIER APPLICATIONS

This application claims the benefit of:
1. U.S. Provisional Patent Application Ser. No. 60/086,329, filed May 21, 1998 by Kwan-Ho Chan for APPARATUS AND METHOD FOR LIGAMENT FIXATION; and
2. U.S. Provisional Patent Application Ser. No. 60/125,745, filed Mar. 23, 1999 by Kwan-Ho Chan for APPARATUS AND METHOD FOR LIGAMENT FIXATION.

FIELD OF THE INVENTION

The present invention relates to surgical apparatus and methods in general, and more particularly to apparatus and methods for fixing a ligament in a bone tunnel.

BACKGROUND OF THE INVENTION

The use of interference screws to fix the ends of a bone-tendon-bone complex to the walls of bone tunnels is well known in the art. It is generally accepted that an interference screw provides sufficient fixation of a bone block in a bone tunnel to allow for early rehabilitation after ligament surgery, such as in anterior cruciate ligament (ACL) reconstruction surgery.

Some techniques avoid using a bone block to fix a ligament in a bone tunnel. Referring to FIG. 1, one such technique involves suspending a ligament L in a bone tunnel C with a pull-through suture S. Over time, the ligament L and surrounding bone grow together, fixing the ligament L in place.

Note: As used herein, the term "ligament L" is meant to refer to the replacement ligament being fixed in a bone tunnel. To that end, the replacement ligament L might comprise:
1. ligament or tendon or other tissue harvested from the patient's own tissue (known as autograft tissue); or
2. ligament or tendon or other tissue harvested from another human donor (known as allograft tissue); or
3. ligament or tendon or other tissue harvested from an animal source (know as xenograft tissue); or
4. ligament or tendon or other tissue made by tissue engineering; or
5. prosthetic ligament made of artificial material; or
6. a combination of the above.

Referring to FIG. 2, another technique uses an interference screw to directly fix ligaments without a bone block (such as a semitendonosis and gracilis tendons) to the walls of the bone tunnel. In this case, the ligament L may be towed into place with suture S, which normally is removed after interference screw fixation has been achieved. However, one disadvantage of direct fixation of the ligament in a bone tunnel with an interference screw is the risk of slippage of the ligament under load prior to the ligament healing to the bone. Such slippage may occur during the rehabilitative period when the ligament is subjected to repetitive loading. To provide for a sufficient interference fit, a large interference screw may be required. However, these large interference screws may cause necrosis of the tendon because of excessive compression of the ligament against the bony tunnel wall.

OBJECTS OF THE INVENTION

One object of the present invention is to provide an improved apparatus and method to augment the interference screw fixation of a ligament in a bone tunnel.

Another object of the present invention is to provide an improved apparatus and method to resist slippage of the ligament in a bone tunnel under cyclic loading.

Yet another object of the present invention is to provide an improved apparatus and method for fixing a ligament in a bone tunnel without excessive sideways pressure on the ligament that may result in tissue necrosis.

SUMMARY OF THE INVENTION

The present invention provides a jamming retainer to augment the interference screw fixation of a ligament in a bone tunnel, whereby resistance to slippage of the ligament under static and cyclic loading is improved. The invention also provides a jamming retainer for fixing a ligament in a bone tunnel without excessive sideways pressure on the ligament that may result in tissue necrosis. The jamming retainer includes a substantially rigid body with a bore or loop for attaching a ligament or tendon to the jamming retainer. The jamming retainer has a bore or ring for receiving a suture for towing the jamming retainer and ligament or tendon through a bone tunnel. Once the jamming retainer and ligament have been positioned within the bone tunnel, e.g., by towing, the ligament is fixed by insertion of an interference screw to compress the ligament sideways against the wall of the bone canal. However, as noted above, fixation achieved solely by engagement of the interference screw against the ligament is sometimes inadequate; however, with the present invention, this fixation is significantly improved through the use of the jamming retainer in one of two ways. In the first mode, sometimes hereinafter referred to as the "blocking mode", the interference screw is advanced into the bone tunnel so as to be just touching, or just short of touching, the jamming retainer. Any subsequent proximal slippage of the ligament will draw the jamming retainer against the distal tip of the interference screw. Further slippage of the ligament is then prohibited by the jamming retainer abutting against the interference screw. In the second mode, sometimes hereinafter referred to as the "sideways compression mode", the interference screw is advanced until the interference screw engages the jamming retainer and pushes the jamming retainer sideways, thus causing the jamming retainer to be partially embedded in the wall of the bone tunnel. Thus, the jamming retainer is fixed in position by its engagement with the interference screw and the wall of the bony tunnel.

BRIEF DESCRIPTION OF THE DRAWINGS

FIGS. 7 and 8 are schematic representations of a tendon, attached to the jamming retainer of FIGS. 3 and 4, drawn into a bone tunnel with a pull-through suture, and secured in the bone tunnel with an interference screw, respectively;

FIG. 27 is a partial sectional view of fixation apparatus formed in accordance with the present invention;

FIG. 28 is a sectional view of a suture retainer portion of the fixation apparatus shown in FIG. 28;

DESCRIPTION OF THE PREFERRED EMBODIMENTS

The present invention works in conjunction with a standard interference screw such as a Bioscrew (made by Linvatec) or an RCI screw (made by Smith and Nephew). The invention provides a jamming retainer which is attached to a ligament. The jamming retainer is positioned in a bone tunnel, and then, preferably, secured relative to the walls of the bone tunnel with an interference screw. More particularly, in one preferred embodiment, the interference screw urges the jamming retainer laterally against, and into, the wall of the bone tunnel. Interference between the jamming retainer and the walls of the bone tunnel fixes the ligament in the bone tunnel without ligament necrosis.

The interference screw also bears some of the load imparted on the jamming retainer by the ligament during normal use of the joint. Thus, even if the interference screw does not create a direct fixation between the jamming retainer and the wall of the bone tunnel, any slippage of the ligament will cause the jamming retainer to abut against the interference screw and thus any further slippage is prohibited. Thus, by closely positioning the jamming retainer and interference screw in the bone tunnel slippage of the ligament can be substantially prohibited. The jamming retainer may bear some or all of the load of the ligament, depending on the degree of direct fixation of the ligament imparted by the interference screw (and depending on the degree of the load carried by the suture).

Figure 2:
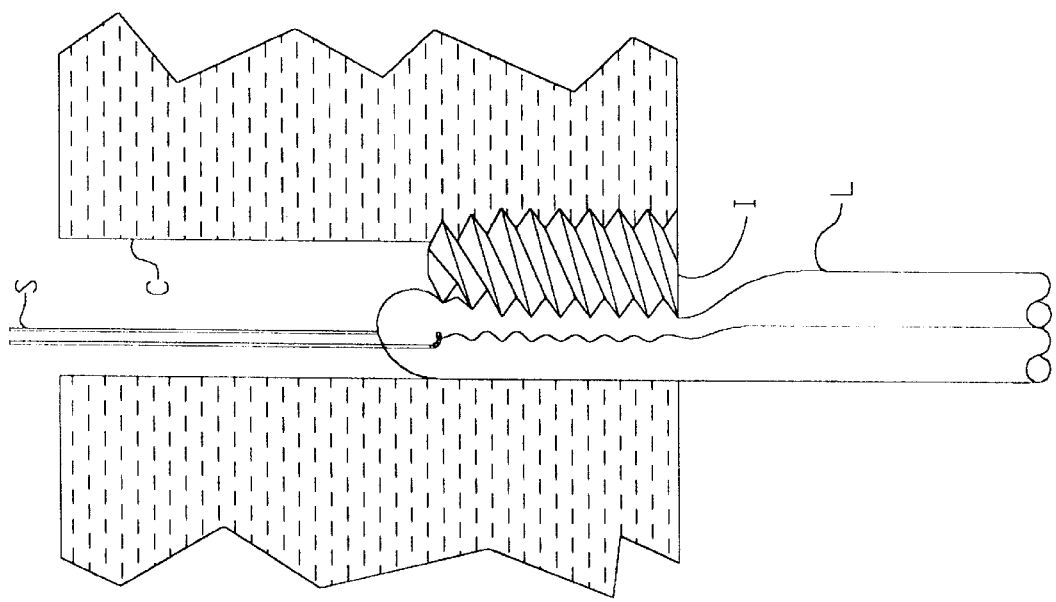
FIG. 2 is a schematic representation of direct fixation of a ligament in a bone tunnel using an interference screw.
Figure 1:
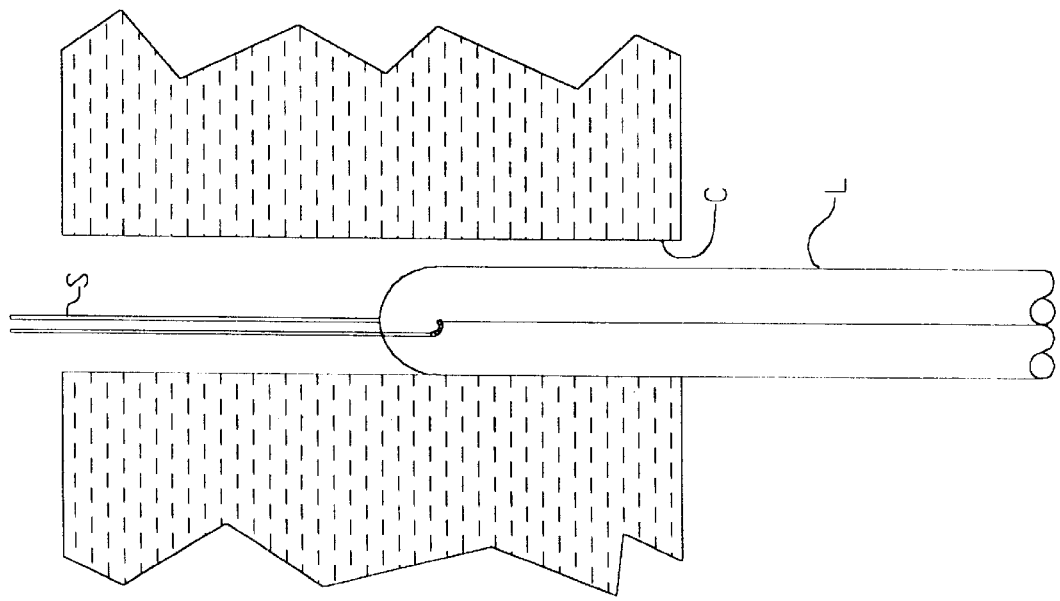
FIG. 1 is a schematic representation of a tendon drawn into a bone tunnel with a pull-through suture.
Figure 3:
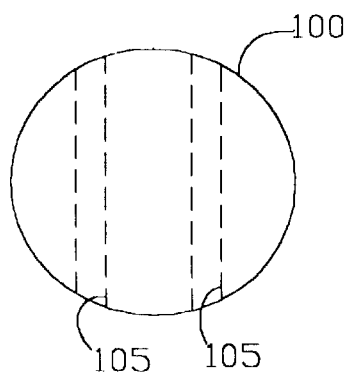
FIGS. 3 and 4 are front elevational, and vertical cross-sectional detail views, respectively, of an embodiment of a jamming retainer.
Figure 4:
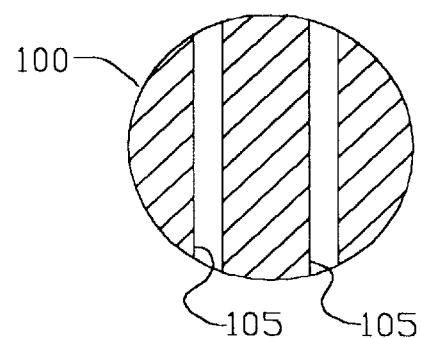
Figure 5:
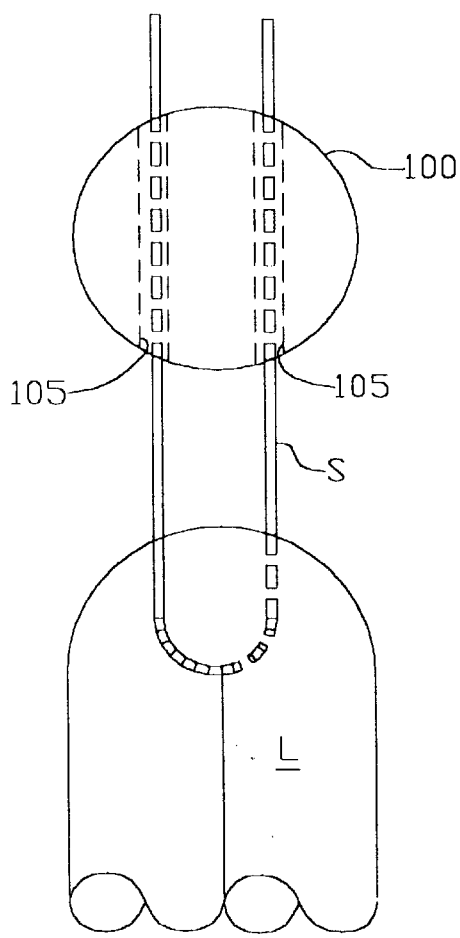
FIGS. 5 and 6 are schematic representations of a tendon being attached, and snugged, respectively, to the jamming retainer of FIGS. 3 and 4.
Figure 6:
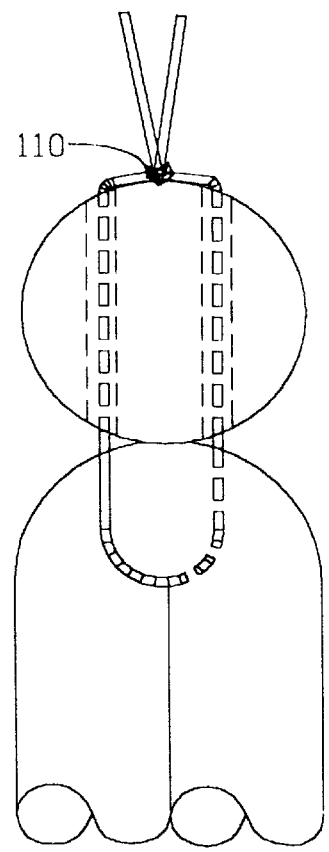

Referring to FIGS. 3 and 4, one embodiment of a jamming retainer 100 is a substantially rigid spherical body with longitudinal bores 105 for receiving suture. As shown in FIGS. 5 and 6, suture S passes through one longitudinal bore 105, encircles a ligament L, and passes through the other longitudinal bore 105. Once the ligament is snugged against the jamming retainer 100, as shown in FIG. 6, the suture is secured with a knot 110.

Referring to FIGS. 7 and 8, once the ligament L and jamming retainer 100 are secured, the ends of the suture S may be used to tow the jamming retainer 100 and ligament L into position in a bone tunnel C. Once positioned, as shown in FIG. 8, an interference screw I traps, secures or fixes the position of the jamming retainer 100 (and thus the ligament L) in the bone tunnel C. In the event that the interference screw I is inserted just short of contact with the jamming retainer 100, the ligament L may slip slightly with load applied to it. The ligament slippage will cause the jamming retainer 100 to migrate towards the interference screw I. Further migration of the ligament L and the jamming retainer 100 is prevented when the jamming retainer 100 abuts against the interference screw I.

The interference screw I encroaches the wall of the bone tunnel C, thus fixing the position of the interference screw I relative to the bone tunnel C. Preferably, the interference screw I is inserted sufficiently far into bone tunnel C to urge the jamming retainer 100 laterally so as to encroach the wall of the bone tunnel C, thus securely fixing the position of the jamming retainer 100 (and hence the ligament L) relative to the bone tunnel C.

Figure 9:
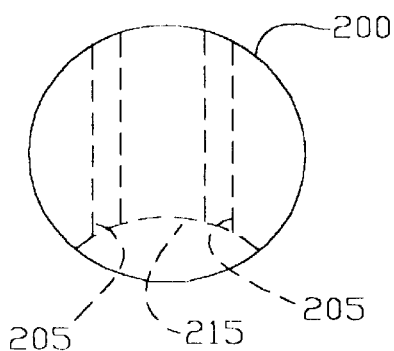
FIGS. 9 and 10 are front elevational, and vertical cross-sectional detail views, respectively, of another embodiment of a jamming retainer.
Figure 10:
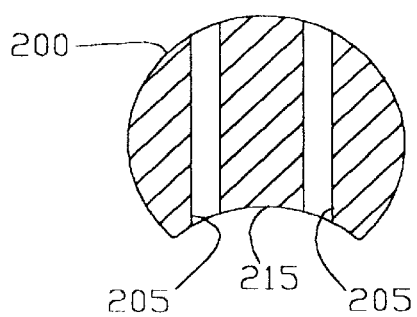
Figure 11:
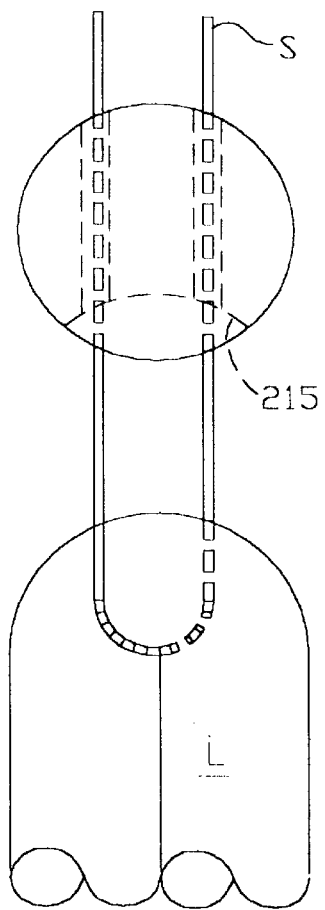
FIGS. 11 and 12 are schematic representations of a tendon being attached, and snugged, respectively, to the jamming retainer of FIGS. 9 and 10.
Figure 12:
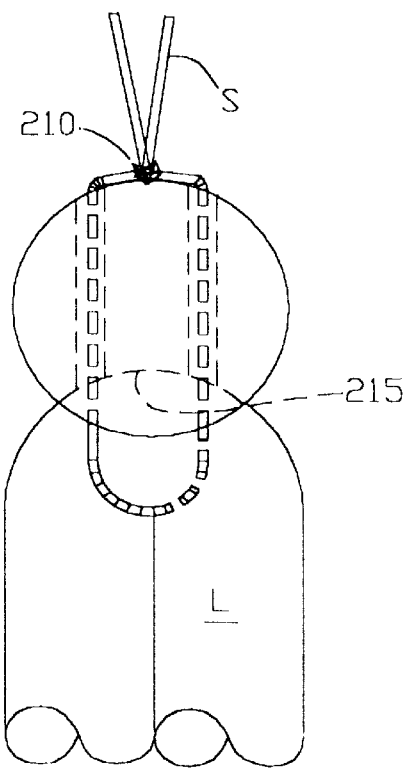

Referring to FIGS. 9 and 10, another embodiment of a jamming retainer 200 is a substantially rigid spherical body with longitudinal bores 205 for receiving suture. As shown in FIGS. 11 and 12, suture S passes through one longitudinal bore 205, encircles a ligament L, and passes through the other longitudinal bore 205. The jamming retainer 200 has a recess 215, which complements the shape of a folded ligament, as shown in FIG. 12. Once the ligament is snugged against the jamming retainer 200, the suture is secured with a knot 210.

Similar to the jamming retainer 100 as shown in FIGS. 7 and 8, once the ligament L and jamming retainer 200 are secured, the ends of the suture S may be used to tow the jamming retainer 200 and ligament L into position in a bone tunnel C. Once positioned, an interference screw I traps, secures or fixes the position of the jamming retainer 200 (and thus the ligament L) in the bone tunnel C.

Figure 13:
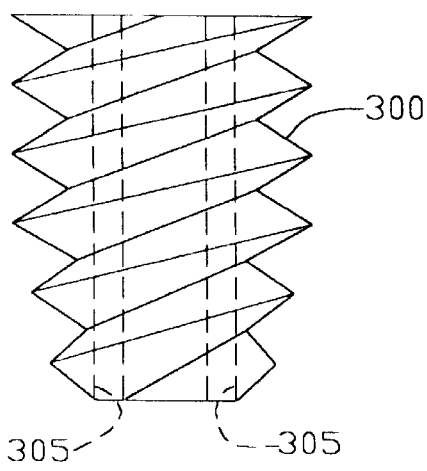
FIGS. 13 and 14 are front elevational, and vertical cross-sectional detail views, respectively, of an additional embodiment of a jamming retainer.
Figure 14:
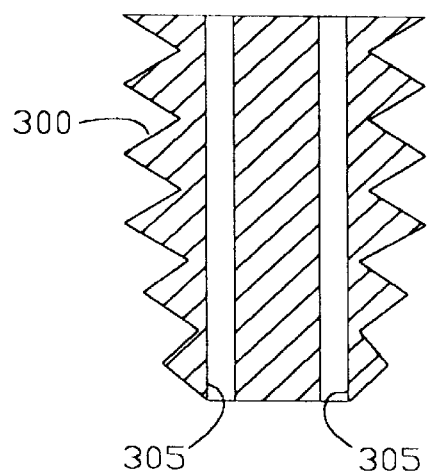
Figure 15:
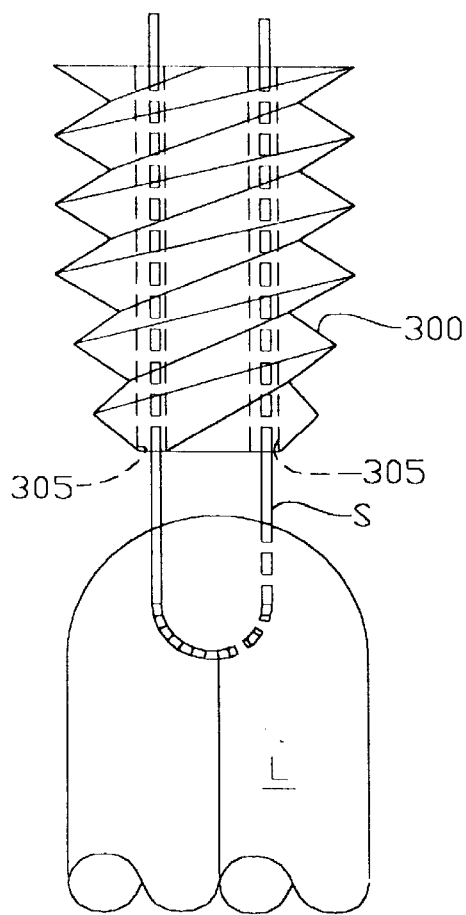
FIGS. 15 and 16 are schematic representations of a tendon being attached, and snugged, respectively, to the jamming retainer of FIGS. 13 and 14.
Figure 16:
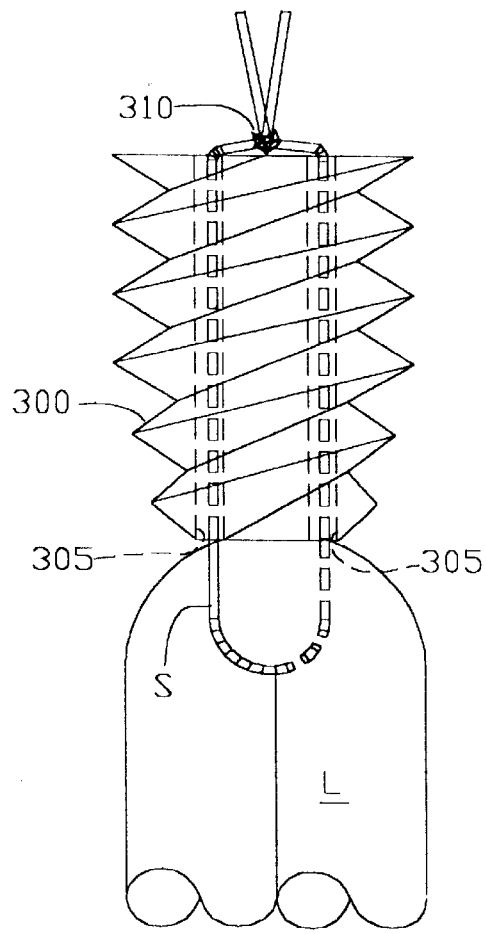

Referring to FIGS. 13 and 14, a further embodiment of the invention is a threaded-body jamming retainer 300 of substantial rigidity with longitudinal bores 305 for receiving sutures. As shown in FIGS. 15 and 16, suture S passes through one longitudinal bore 305, encircles a ligament L, and passes through the other longitudinal bore 305. Once the ligament is snugged against the jamming retainer 300, as shown in FIG. 16, the suture is secured with a knot 310.

Figure 18:
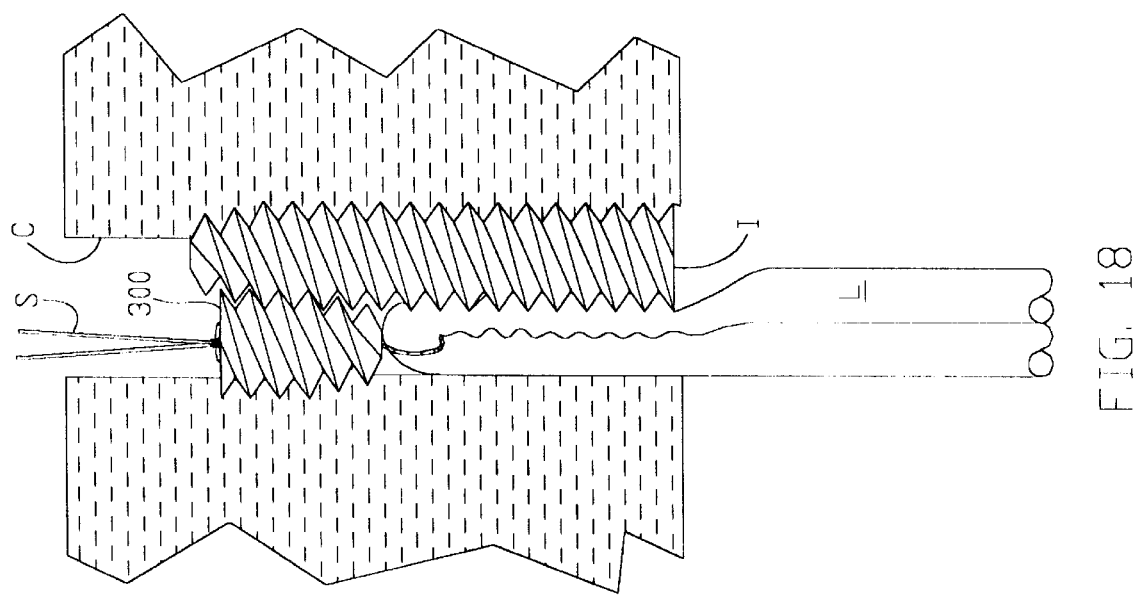
FIGS. 17 and 18 are schematic representations of a tendon, attached to the jamming retainer of FIGS. 13 and 14, drawn into a bone tunnel with a pull-through suture, and secured in the bone tunnel with an interference screw, respectively.
Figure 17:
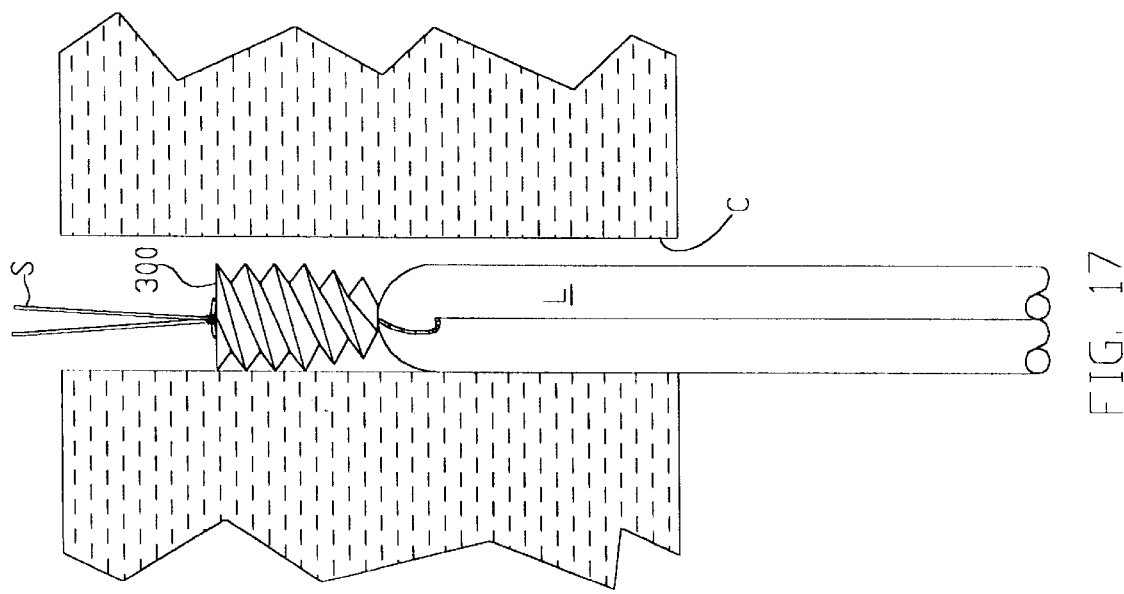

Referring to FIGS. 17 and 18, once the ligament L and jamming retainer 300 are secured, the ends of the suture S may be used to tow the jamming retainer 300 and ligament L into position in a bone tunnel C. Once positioned, an interference screw I traps, secures or fixes the position of the jamming retainer 300 (and thus the ligament L) in the bone tunnel C. In one preferred embodiment of the invention, the geometry of the threads of jamming retainer 300 corresponds to the geometry of the threads of interference screw I, whereby jamming retainer 300 and interference screw I can be intermeshed with one another (e.g., in the manner shown in FIG. 18) if so desired.

One modification of the present invention is the provision of one or more transverse holes or loops in the jamming retainer, through which the ligament and/or sutures can be threaded. In this case, retaining sutures and the suture retainer (see FIGS. 27–30) would not be required.

Figure 19:
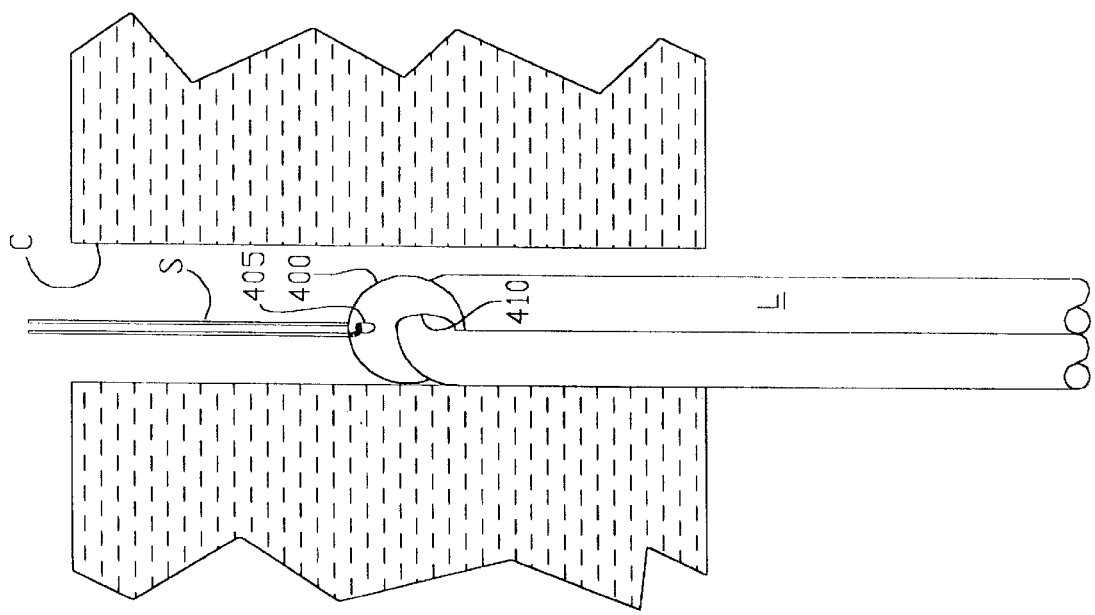
FIG. 19 is a schematic representation of an alternate embodiment for a spherical jamming retainer.

Such an alternative embodiment is shown in FIG. 19, where the jamming retainer 400 is in the form of a sphere, and where a bore 405 in the upper part of the sphere is provided for engagement of the pull-through suture S. The ligament L is passed through a bore 410 (or a loop, described below) that is incorporated as part of the retainer 400.

Figure 20:
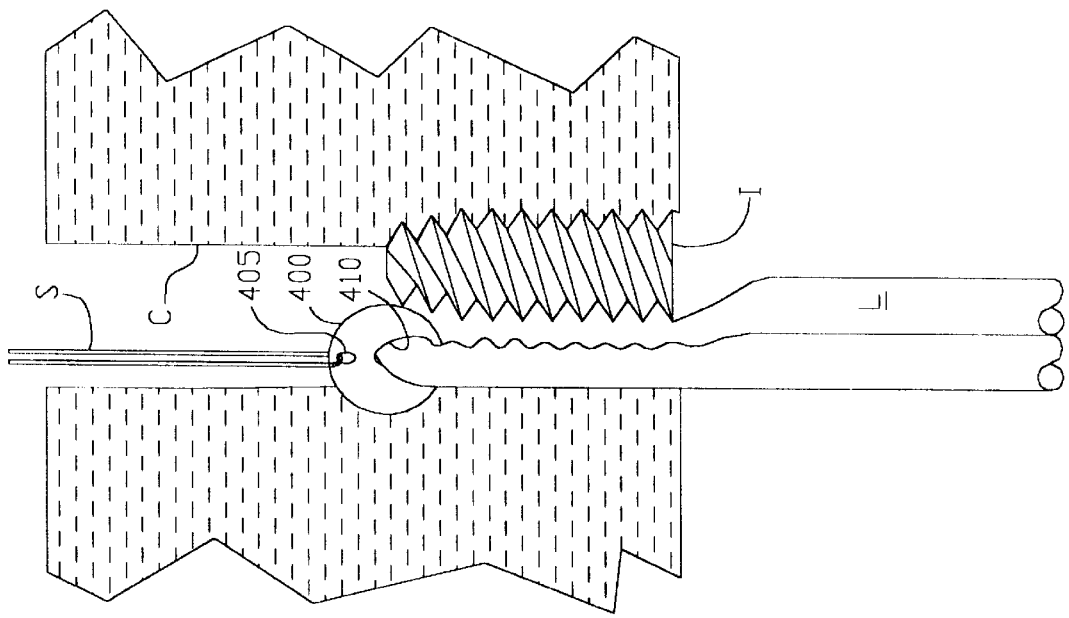
FIG. 20 is a schematic representation of an alternate embodiment for a spherical jamming retainer enhancing fixation of a ligament using an interference screw.

When the interference screw I is advanced, as shown in FIG. 20, it will push the spherical retainer 400 sideways and cause it to be partially embedded in the soft cancellous bone of the bone tunnel C. Alternatively, advancement of interference screw I may be stopped short of causing lateral movement of spherical retainer 400, in which case interference screw I will simply trap the spherical retainer in the bone tunnel.

Figures 21, 22:
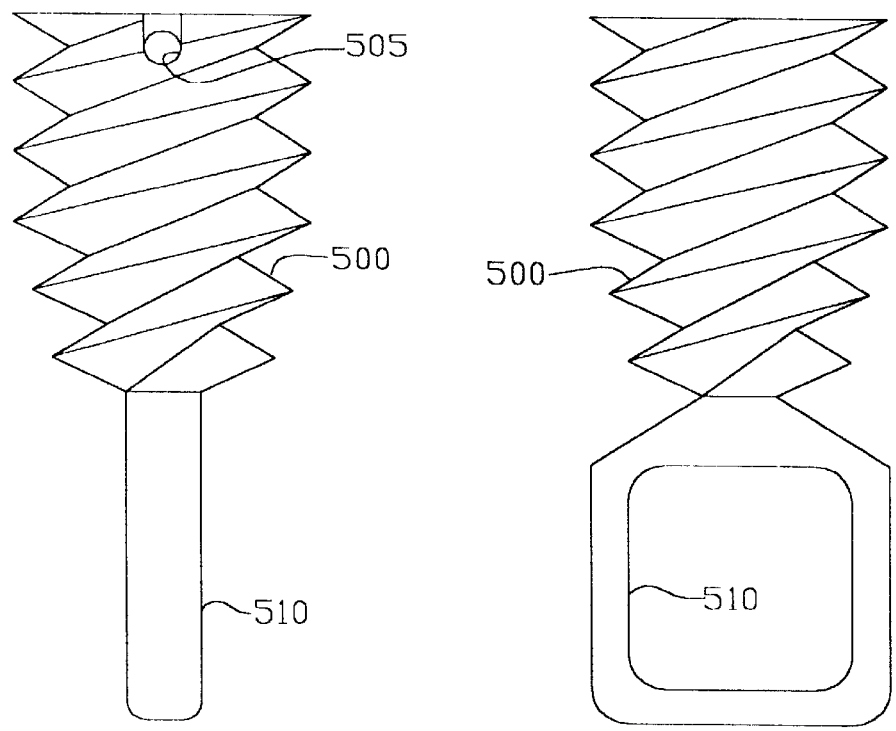
FIG. 21 is a front view of an alternate embodiment for a jamming retainer with an incorporated retaining loop.
FIG. 22 is a side view of an alternate embodiment for a jamming retainer with an incorporated retaining loop.

Referring to FIGS. 21 and 22, an additional embodiment of the present invention provides a threaded-body jamming retainer 500 of substantial rigidity, where a bore 505 in the upper part of the jamming retainer 500 is provided for engagement of a pull-through suture (not shown). A ligament (also not shown) is passed through a bore 510 incorporated as part of the retainer 500.

Figure 23:
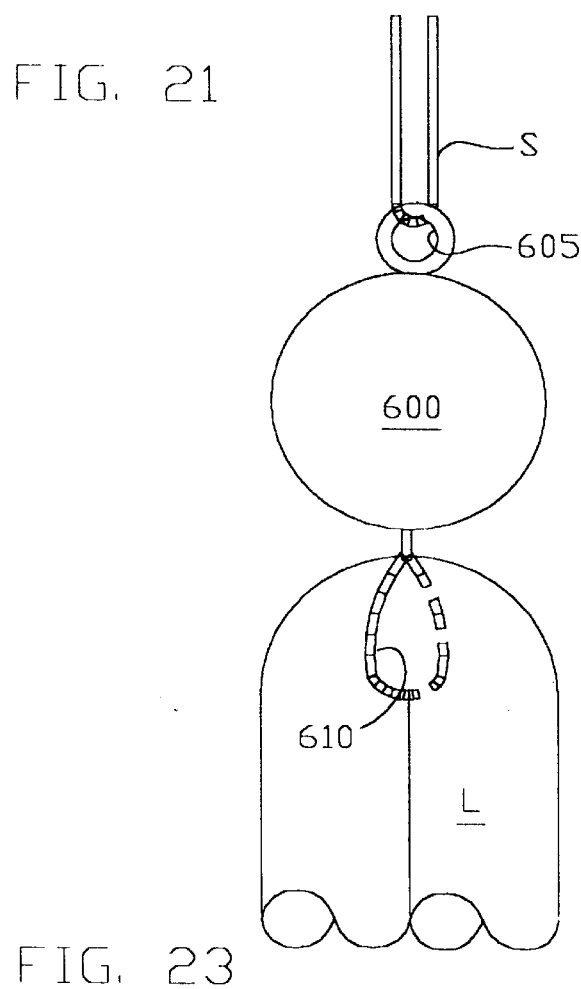
FIG. 23 is a schematic side view of a spherical jamming retainer with a loop for a pull-through suture, and a retaining loop, incorporated therewith.

Referring to FIG. 23, another embodiment of the invention includes a spherical jamming retainer 600, where a ring 605 in the upper part of the jamming retainer 600 is provided for engagement of a pull-through suture S. A ligament L is passed through a loop 610 incorporated as part of the retainer 600.

Figures 24, 25:
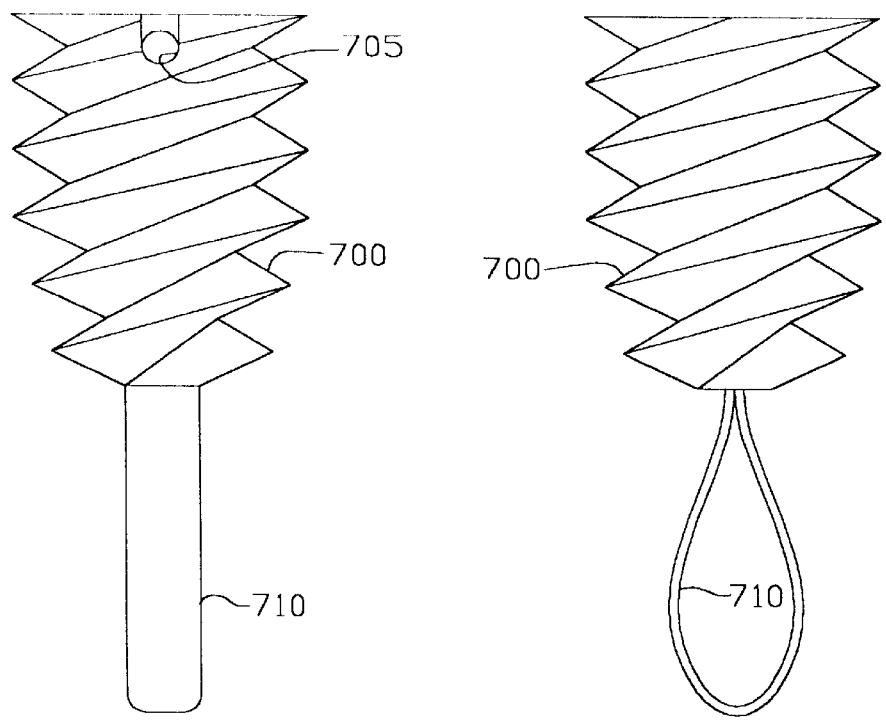
FIG. 24 is a front view of an alternate embodiment for a jamming retainer with an incorporated retaining loop.
FIG. 25 is a side view of an alternate embodiment for a jamming retainer with an incorporated retaining loop.

Referring to FIGS. 24 and 25, an additional embodiment of the invention provides a threaded-body jamming retainer 700 of substantial rigidity, where a bore 705 in the upper part of the jamming retainer 700 is provided for engagement of a pull-through suture (not shown). A ligament (also not shown) is passed through a loop 710 incorporated as part of the retainer 700.

Figure 26:
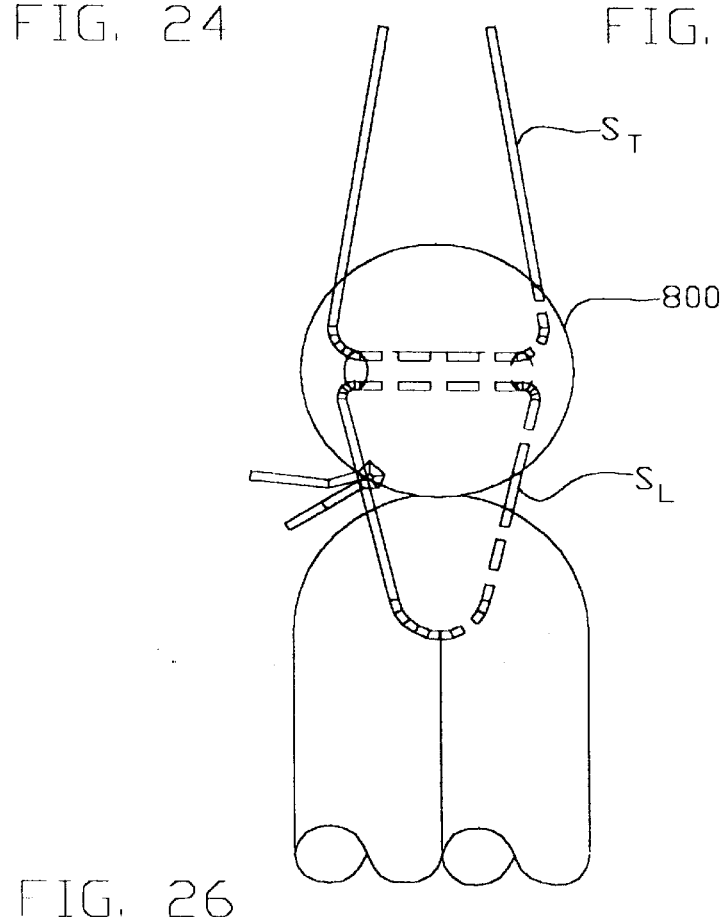
FIG. 26 is a schematic side view showing a spherical jamming retainer with transverse bores for passage of sutures.

The ligaments may be tied to yet another embodiment of a jamming retainer 800, shown in FIG. 26. A suture $S_T$ is used for towing the jamming retainer 800 through a bone tunnel. A suture $S_L$ is used for retaining a ligament L to the jamming retainer 800.

In another form of the invention, a jamming retainer 900 includes two parts: a substantially rigid threaded body 905 and a suture retainer part 910, both shown in FIG. 27. The threaded body 905 is tapered externally on one end 915. The external threads have the same pitch as a mating interference screw I (shown in FIG. 30). The threaded body 905 has a partially tapered bore 920 complementary to the tapered body 925 of the suture retainer part 910 (FIG. 28). The partially tapered bore is widest at the end 930 opposite to the externally tapered end 915. The suture retainer part 910 has a tapered body 925 to fit inside the partially tapered bore 920 of the threaded body 905. A ring part 935 (FIGS. 27 and 28) is for retaining suture $S_L$ tied to the ligament L. One or two #2 sutures maybe used. The ring part 935 is also for passage of the pull-through suture $S_T$.

It should be noted that the complementary taper of the bore 920 of the threaded body 905, and the tapered body 925 of the suture retainer 910, helps to protect the knot 940 of the retaining suture $S_L$. Tension in the suture $S_L$ distal to the tip of tapered body 905 will tend to draw the suture retainer 910 farther into the tapered bore 920. This will cause increased binding of the portion of the suture $S_L$ as it is squeezed between the wall of the tapered body 910 and the wall of the tapered bore 920, thus resisting slippage of the suture $S_L$ and protecting the knot 940.

Figure 30:
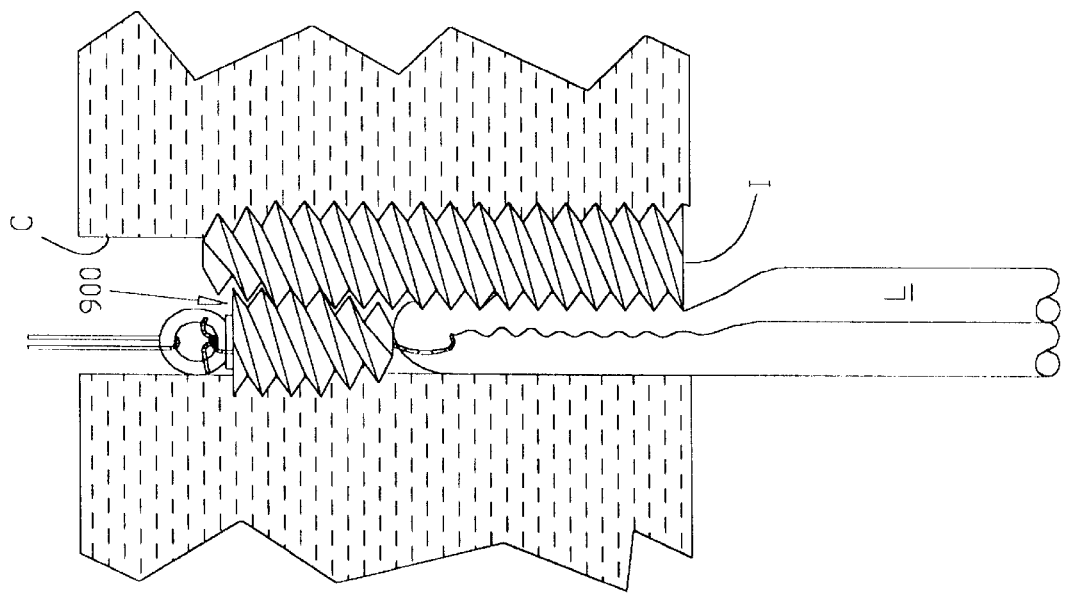
FIG. 30 is a schematic representation of the present invention enhancing fixation of a ligament using an interference screw.
Figure 29:
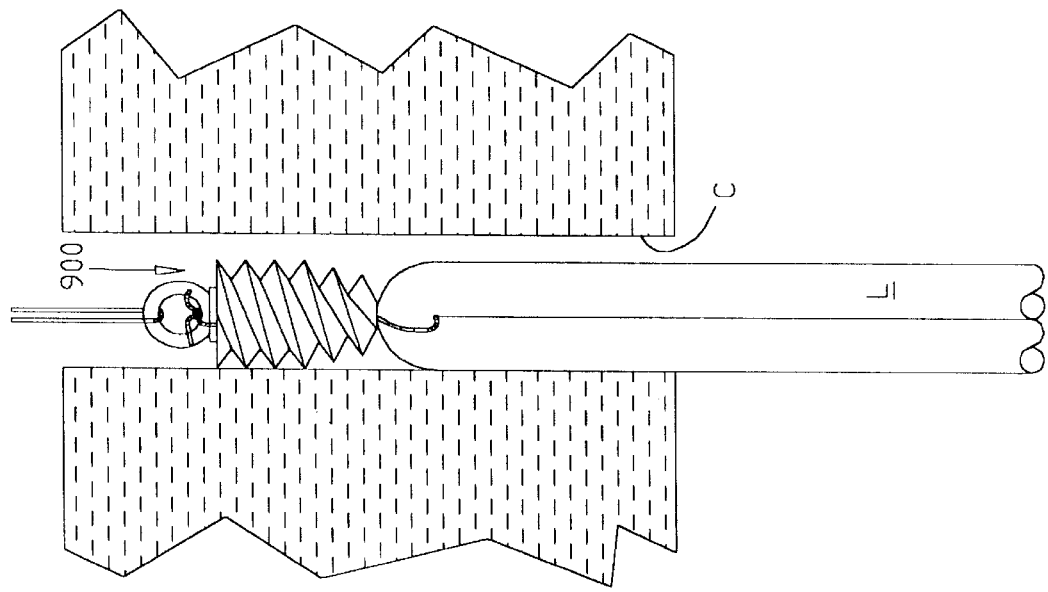
FIG. 29 is a schematic representation of a tendon attached to a fixation device and drawn into a bone tunnel with a pull-through suture.

Referring also to FIGS. 29 and 30, as the interference screw I is advanced from below, it first engages the ligament L, compressing it against the wall of the bone tunnel C. The interference screw I also engages the wall of the bone tunnel C, both by threading mechanics and also by compression of the cancellous bone of the bone tunnel C. As the interference screw I is advanced farther, it engages the threaded body of the jamming retainer 900. As the combined width of the interference screw and the jamming retainer is much larger than the diameter of the bone tunnel C, the advancing interference screw I pushes the jamming retainer 900 sideways. As the jamming retainer 900 is urged sideways, the threads in the threaded body 905 become embedded in the cancellous bone of the bone tunnel C. The engagement of the jamming retainer with the wall of the bone tunnel C, and with the threads of the interference screw I, enhances the fixation of the ligament L via the retaining sutures $S_T$ and $S_L$.

The two disadvantages of the two-piece jamming retainer 900 are:

1. valuable surgery time is taken up in tying the retaining sutures; and
2. the knots may loosen.

Thus, it is advantageous during manufacture to provide a means for engaging the ligament. This can be in the form of a transverse bore, as shown in FIG. 19, or in the form of a bore or loop incorporated as part of the jamming retainers, as shown in FIGS. 21–25. The bore can be an integral part of the jamming retainer, as shown in FIGS. 21 and 22. A flexible loop made of suture material such as Dacron or other suture material can be incorporated into the retainer during manufacture of the retainer of FIGS. 23–25.

The jamming retainer can be made of metal, plastic or bioabsorbable materials.

Although the threaded cylindrical shape, and the non-threaded spherical shape, of the jamming retainer are illustrated here, jamming retainers of other shapes are also possible.

Although the various embodiments of jamming retainer have been shown to have different shapes, it is to be appreciated that all the embodiments disclosed will function both in the blocking mode and in the sideways compression mode so as to enhance fixation of the ligament L in the bone tunnel.

Figure 31:
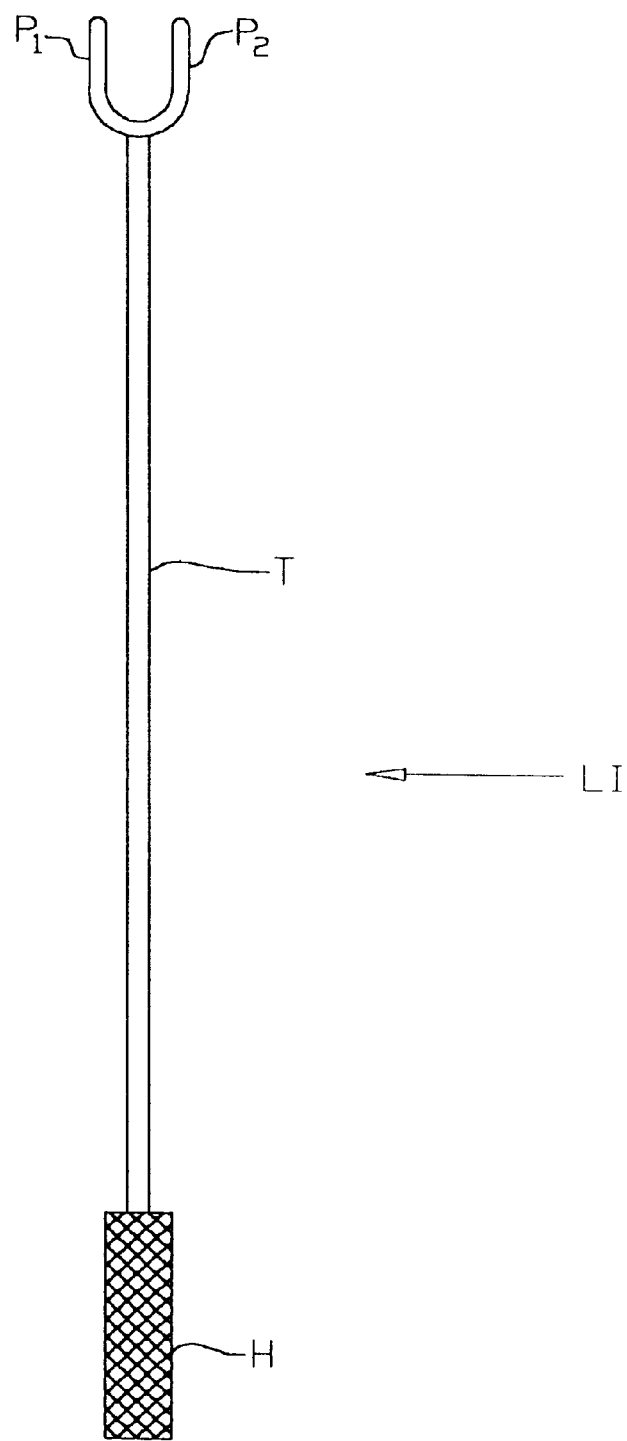
FIG. 31 is a side elevational view of a ligament inserter.
Figure 32:
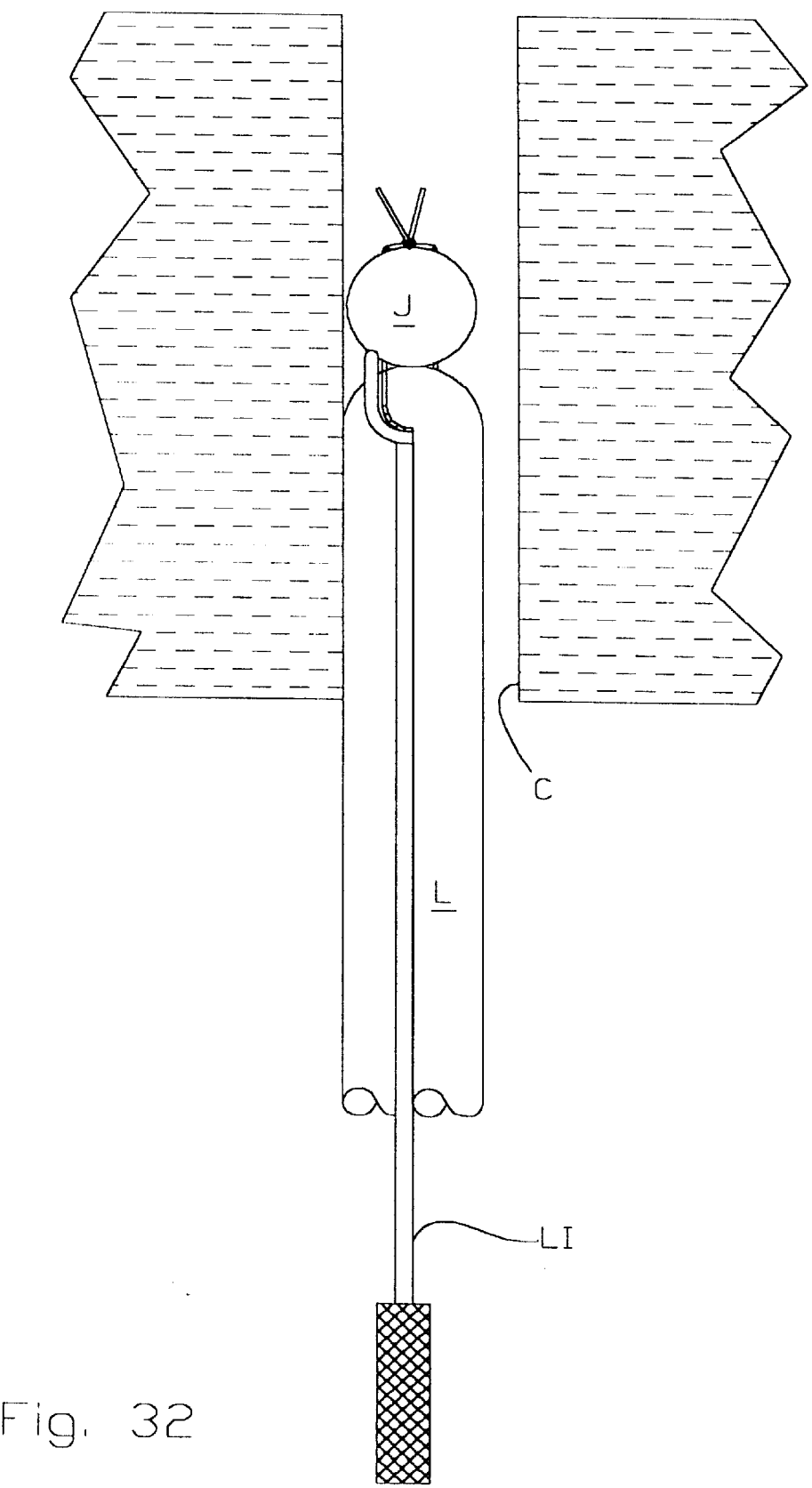
FIG. 32 is a schematic representation of a ligament inserter inserting a ligament attached to a jamming retainer into a bone tunnel.

Referring to FIGS. 31 and 32, rather than towing a jamming retainer and ligament into position, which necessitates additional incisions and increased drilling, the jamming retainer and ligament may be pushed into position with a ligament inserter LI. The ligament inserter LI comprises a handle H, a slender shaft T and means for engaging the jamming retainer or the distal portion of the ligament. The ligament inserter LI uses prongs $P_1$ and $P_2$ for maintaining the jamming retainer or ligament during insertion of the jamming retainer and ligament in a bone tunnel. As shown in FIG. 32, the ligament L, having been attached to a jamming retainer J, is urged with the jamming retainer through a bone tunnel C. The jamming retainer may then be secured in the bone tunnel using an interference screw in the manner previously discussed.

What is claimed is:

1. An apparatus for augmenting an interference screw fixation of a ligament in a bone tunnel, wherein the interference screw engages a wall of the bone tunnel and engages the ligament in the bone tunnel, and whereby resistance to slippage of the ligament is improved, said apparatus comprising a jamming retainer adapted to retain the ligament, said jamming retainer being adapted for disposition in the bone tunnel, distally of the ligament, and such that upon disposition of the interference screw to lock the ligament in the bone tunnel, said jamming retainer is adapted to be engaged by the interference screw to prevent proximal migration of said jamming retainer, said jamming retainer being substantially rigid, said jamming retainer having a recess adapted to complement a shape of the ligament.

* * * * *